United States Patent [19]

Boyd et al.

[11] Patent Number: 6,001,772
[45] Date of Patent: *Dec. 14, 1999

[54] PESTICIDE AND METHOD OF MAKING AND USING SAME

[75] Inventors: Larry C. Boyd, Wellton, Ariz.; Truman V. Sylling, El Centro; Stephen L. Allen, San Diego, both of Calif.

[73] Assignee: Sotac Corporation, El Centro, Calif.

[ * ] Notice: This patent is subject to a terminal disclaimer.

[21] Appl. No.: 09/012,994

[22] Filed: Jan. 26, 1998

Related U.S. Application Data

[63] Continuation of application No. 08/671,042, Jun. 27, 1996, Pat. No. 5,712,224, which is a continuation-in-part of application No. 07/993,605, Dec. 21, 1991, abandoned, which is a continuation of application No. 07/711,911, Jun. 7, 1991, abandoned, which is a continuation-in-part of application No. 07/709,837, Jun. 4, 1991, abandoned, which is a continuation-in-part of application No. 07/520,104, May 4, 1990, Pat. No. 5,106,406, which is a division of application No. 07/068,026, Jun. 29, 1987, Pat. No. 4,923,500, which is a continuation-in-part of application No. 07/732,501, May 9, 1985, Pat. No. 4,687,505, which is a continuation-in-part of application No. 07/547,866, Nov. 2, 1983, abandoned.

[51] Int. Cl.⁶ .................................................. A01N 25/00
[52] U.S. Cl. ...................... 504/116; 47/DIG. 10; 71/DIG. 1; 424/405
[58] Field of Search .............................................. 504/116

[56] References Cited

U.S. PATENT DOCUMENTS

| | | | |
|---|---|---|---|
| 2,751,368 | 6/1956 | Yost et al. | 260/41 |
| 3,029,140 | 4/1962 | Hemwall | 71/33 |
| 3,091,522 | 5/1963 | Hemwall | 71/1 |
| 3,554,987 | 1/1971 | Smith | 260/79.3 |
| 3,810,834 | 5/1974 | Jones et al. | 210/58 |
| 3,897,209 | 7/1975 | Harris et al. | 21/2.7 R |
| 3,900,378 | 8/1975 | Yen et al. | 71/903 X |
| 3,958,972 | 5/1976 | Magin | 71/27 |
| 3,963,636 | 6/1976 | Harris et al. | 252/181 |
| 4,007,258 | 2/1977 | Cohen et al. | 71/DIG. 1 |
| 4,070,178 | 1/1978 | Johnson et al. | 504/352 |
| 4,089,796 | 5/1978 | Harris et al. | 252/181 |
| 4,098,814 | 7/1978 | Sommer et al. | 260/502.5 |
| 4,303,438 | 12/1981 | Zaslavsky et al. | 71/903 X |
| 4,388,102 | 6/1983 | Purdum | 504/206 |
| 4,396,412 | 8/1983 | Heller et al. | 71/27 |
| 4,687,505 | 8/1987 | Sylling et al. | 71/27 |
| 4,808,215 | 2/1989 | Gill et al. | 71/105 |
| 4,923,500 | 5/1990 | Sylling et al. | 71/27 |
| 5,047,078 | 9/1991 | Gill | 71/11 |
| 5,712,224 | 1/1998 | Boyd et al. | 504/116 |

FOREIGN PATENT DOCUMENTS

| | | |
|---|---|---|
| A0203734 | 4/1986 | European Pat. Off. . |
| A0300947 | 1/1989 | European Pat. Off. . |
| 80/06714 | 11/1986 | WIPO . |
| WO-A-86/06714 | 11/1986 | WIPO . |
| WO-A-89/00155 | 12/1986 | WIPO . |
| WOA8900155 | 12/1986 | WIPO . |

OTHER PUBLICATIONS

Deubin, Leonard, "The Effect of Organophosphorus Compounds and Polymers on $CaCO_3$ Crystal Morphology," *Journal of the Cooling Institute*, vol. 3, No. 1, Winter 1982, p. 17 et seq.

Belclene 200 Descriptive Brochure of the Water Chemicals Group of CIBA–GEIGY Corporation including Product Application Bulletin No. 1 and Belclene 210 descriptive material.

Farm Chemicals Handbook, 1991, pp. c–196–197.

*Primary Examiner*—S. Mark Clardy
*Attorney, Agent, or Firm*—Woodcock Washburn Kurtz Mackiewicz & Norris, LLP

[57] ABSTRACT

A weed eradicating substance, and a desalination substance. A method of use includes irrigating the soil with water, prior to planting, to cause the germination of weed seeds, and thereafter applying a desalination agent to increase weed seed germination. An application of the inventive pesticide then causes a much larger number of weeds to be eradicated.

9 Claims, No Drawings

PESTICIDE AND METHOD OF MAKING AND USING SAME

CROSS REFERENCE TO RELATED APPLICATION

This Application is a continuation under 37 C.F.R. §1.53 (b) of or application Ser. No. 07/671,042, filed Jun. 27, 1996, now U.S. Pat. No. 5,712,224 which is a Rule 1.62 continuation-in-part of application Ser. No. 07/993,605, filed Dec. 21, 1991 (now abandoned), which is a continuation of application Ser. No 07/711,911, filed Jun. 7, 1991 (now abandoned), which is a continuation-in-part of application Ser. No. 07/709,837, filed Jun. 4, 1991 (now abandoned), which is a continuation-in-part of application Ser. No. 07/520,104, filed May 4, 1990 (now issued U.S. Pat. 5,106,406), which is a division of application Ser. No. 07/068,026, filed Jun. 29, 1987 (now issued U.S. Pat. 4,923,500), which is a continuation-in-part of application Ser. No. 07/732,501, filed May 9, 1985 (now issued U.S. Pat. 4,687,505), which is a continuation-in-part of application Ser. No. 07/547,866, filed Nov. 2, 1983 (now abandoned). The parent patent applications are hereby incorporated by reference as if fully set forth herein.

TECHNICAL FIELD

This invention relates generally to soil pesticide compositions and a method of making and using such compositions. The invention more particularly relates to an improved pesticide composition and method of making and using the same for improving the ability of plants to proliferate soils, in a more effective manner.

BACKGROUND ART

The presence of salts, and other unwanted substances, in soils, such as agricultural soils, and their adverse effects on plant proliferation, have long been recognized. The salts, such as chlorides, carbonates and sulfates of sodium, potassium, calcium and magnesium, are often already present in the soil, prior to planting. In addition, in some cases, salts are introduced into the soil through the use of irrigation water.

In general, the effect of salts on plants is indirect. In this regard, the salts adversely affect osmotic water potential with a resulting reduction in uptake of water by germinating seeds and the roots of established plants. The presence of salts in soils can result in a fewer number of seeds becoming properly established. Also, there can be an undesirable delayed rate of seed establishment, as well as an impairment in the growth of established plants.

Due to such severe adverse effects of salts on plants, it has been long recognized that compositions and methods of using the same, capable of reducing such adverse influences would have great utility. Important advances in the art are the methods and compositions disclosed in U.S. Pat. Nos. 4,687,505 and 4,923,500, as well as in the foregoing mentioned U.S. patent applications.

With regard to the above mentioned patents, there is disclosed techniques for the application of certain anionic materials, or their substantially neutral water soluble salts, to soil in minute amounts, for reducing the harmful effects of salts which had accumulated in the soil from irrigation water, or which were previously present in the soil. In this manner, salts were leached from the soil by the application of a liquid, such as irrigation water. These patented compositions are effective because large areas of soil are treated, prior to planting, by the addition of the anionic materials to irrigation water or by other methods of application applied to the fields generally.

Such patented methods and compositions are highly effective in reducing soil salinity, and have proven to increase plant proliferation and quality as well as increased yield when used in crop production. Of course, other soil conditioning products are required to facilitate plant growth. Water and fertilizer are also used to help plant proliferation. Such substances help to nourish the plants, so that they can grow in a healthy and vigorous manner. However, in some situations, conventional fertilizers may not be entirely satisfactory for facilitating adequate nourishment uptake by plants. In such situations, the plants may not be able to thrive in a vigorous and healthy manner, even when conventional fertilizers are applied. In order to overcome such an inadequate nourishment problem, improved fertilizers have been developed. For a description of such an improved fertilizer, reference may be made to the foregoing U.S. patent application, Ser. No. 709,837, filed Jun. 4, 1991.

In addition to the foregoing mentioned impediments of unwanted salt and inadequate nourishment uptake, the presence of weeds and germinating weed seeds in soil, such as agricultural soils, can cause an adverse affect on plant proliferation. The weeds, and weed seeds, are often already present in the soil, prior to planting. Subsequent to planting, when irrigation water and fertilizers are applied, the weeds compete with the desired plants and, in general, can rob the desired plants of nutrients necessary for root establishment and healthy plant growth. Thus, weeds directly compete with the desired plants for the assimilation of essential nourishment, and the presence of weeds and weed seeds can cause directly the reduction of the quantity, and the quality, of the desired plants.

In addition, at the time of harvesting, the presence of the unwanted and undesirable weeds presents more difficulties for the grower. In this regard, methods have to be adopted for either removing the weeds before harvesting, or for removing the weeds from the crop, after harvesting. The weed removal is often labor intensive and, as a result, both expensive and time consuming.

In view of the foregoing, it is clear that the presence of weeds and weed seeds, in agricultural or other planting soils, can cause substantial economic loss to growers, both by reduction of yields and by increased labor costs for weed removal. Thus, it has long been recognized that compositions and methods for weed control have significant economic value. Because of the well recognized need for such compositions and methods, various herbicidal compositions have been developed. In some cases, when such a composition is applied properly to a moist soil, the liquid is converted into a gaseous in-ground fumigant for controlling both weeds and germinating weed seeds. In addition, some known herbicides have utility for controlling nematodes and other soil-borne diseases such as Rhizoctonia, which also, of course, adversely impact plant growth.

Prior known herbicides, and conventional methods of using them, are effective in reducing weed populations in soils and thereby increasing plant proliferation and plant quality, as well as increased yield. However, for some applications and under certain growing conditions, these known herbicides have not performed in an entirely satisfactory manner. Thus, for a variety of reasons, more effective herbicides for the control of weeds and weed seeds in planting soil is highly desirable.

In order to illustrate the problem, it is well recognized by those skilled in the art that some weeds, especially nutgrass, are especially difficult to control. It has been found, for example, that even after a proper application of a known herbicide to agricultural soils, the number of weeds eradicated generally does not exceed approximately 80 percent. Thus, in many instances, about 20 percent of the weeds remain in the field, after conventional herbicide treatment. Such a percentage of a remaining number of weeds, is known to be undesirable and unwanted in many agricultural growing situations. In this regard, with such a high percentage of the weeds surviving, the desired crop is often so adversely affected that the crop yield and quality are generally acceptable.

In view of the foregoing, it would be highly desirable to have an improved pesticide, which will serve as a more effective composition eradicated weeds and weed seeds to facilitate increased plant proliferation. In addition, it would be highly advantageous to facilitate significantly, the early, as well as effective, eradicated and control of weeds so that a much higher percentage of weeds can be killed. In this regard, such a product would be most effective for early and rapid weed and weed seed control, thereby facilitating early root establishment and nutrient uptake in desirable plants.

Such an improved pesticide and method of using it, would serve to control more quickly and effectively the proliferation of weeds competing for nourishment with the desired plants. With such a more rapid and effective weed controlling composition and method of using it, the desired plants can proliferate more readily, since it is important for the germination and establishment of plants to become properly nourished immediately with as little interference as possible from adverse influences, such as weeds.

DISCLOSURE OF INVENTION

Therefore, it is the principal object of the present invention to provide a new and improved pesticide and methods of making and using it, for enhanced weed eradicated to help proliferate healthy and vigorous plant growth, even in growing conditions not completely advantageous to plant growth.

Another object of the present invention is to provide such a new and improved pesticide and methods of making and using it, for early plant establishment in soils, in an effective and economical manner.

Briefly, in accordance with the present invention, there is provided an improved pesticide and a method of making and using it, to control rapidly the eradication of weeds and weed seeds, thereby enhancing desired plant proliferation and supporting a more efficient harvesting operation.

The pesticide includes a weed eradicating substance, and a desalination substance. A method of use includes irrigating the soil with water, prior to planting, to cause the germination of weed seeds, and thereafter applying a desalination agent to increase weed seed germination. An application of the inventive pesticide then causes a much larger number of weeds to be eradicated.

In one form of the invention, a surfactant is also employed to improve the speed of the effectiveness of the inventive composition in the weed eradication process.

The composition and methods of the present invention present several significant advantages, and unexpected results. In the first place, the eradication of weeds and weed seeds in agricultural soils is substantially increased, thereby enabling the growth of more abundant and healthier crops. In addition, a more uniform plant distribution is achieved, thereby leading to a more efficient, and thus less costly, harvesting operation. Thus, because of the enhanced effectiveness of the pesticide and its method of use, substantial overall cost savings are realized.

BEST MODE FOR CARRYING OUT THE INVENTION

In accordance with the present invention, there is provided a novel pesticide composition which, in use, produces unexpected results. The composition includes a weed and weed seed eradicating substance in combination with a soil desalination substance.

In a preferred form of the present invention, the inventive pesticide is as follows:

300.71 parts by volume VAPAM soil fumigant
1.752 parts by volume polymaleic acid
1.0 parts by volume surfactant
4.767 parts by volume water In the preferred form of the invention, the first ingredient is in the form of a pesticidal composition, sold under the trademark VAPAM, registered in the United States by ICI Group Companies. The remaining three ingredients are in the form of a soil desalination composition sold under the trademark SPER SAL, registered in the United States by Sotac Corporation, having a place of business at El Centro, Calif.

The pesticide of the present invention may be used by soil injection techniques where the substance is injected into a prepared soil followed by watering. In addition, the pesticide may be distributed, together with water, through a sprinkler system or by means of field flood irrigation.

VAPAM is a water soluble liquid which, after application to agricultural soils is converted into a gaseous fumigant. The fumigant is effective in destroying weeds and weed seeds. After a suitable period of time, all of the VAPAM gas dissipates from the soil and the soil is ready for planting.

VAPAM is generally available in a liquid comprised of 32.7% sodium methyldithiocarbamate (anhydrous) and 67.3% inert ingredients. The pesticide is a water soluble liquid which, when applied in a conventional manner to agricultural soil, the liquid is converted into a gaseous fumigant. In time, the gas dissipates from the soil leaving the soil ready for planting. The product has utility in controlling and eradicating various weeds and their germinating weed seeds, unwanted grasses and, in addition, pests such as nematodes, centipedes and certain soilborne diseases, including root fungus. Thus, VAPAM has utility as a pesticide, fungicide, nematicide, insecticide and disease control agent.

The polymaleic acid is an anionic polymer having a molecular weight from about 300 to about 5,000; and the surfactant is triethanolaminedodecylbenzenesulfonate.

The surfactant, preferably an anionic surfactant, is a surface active compound which is capable of lowering surface tension of an aqueous solution. In use, the surfactant spontaneously forms micelles, aggregates of a plurality of surfactant molecules generally having polar head groups on the outside and nonpolar tails buried on the inside. The micellar structure satisfies the salvation requirements of both the polar head groups, which are close to water, and the nonpolar tails which associate with each other on the inside of the micecelle. Thus, the surfactant helps to disperse the salt and in combination with the water, to facilitate micronutrient uptake into plants, thereby leading to early root establishment and increased plant yield.

The following example is given to aid in understanding the invention, but it is to be understood that the particular procedures, conditions or materials of the example are not intended as limitations of the present invention. As more particularly discussed below, use of the inventive composition resulted in a significantly increased eradication of weeds, improved crop yield, and a substantially more uniform crop plants of same size growth and development as compared to a field untreated with the inventive composition.

EXAMPLE 1

1 part by volume SPER SAL 40 parts by volume VAPAM.

The following experiment was conducted on an 18 acre field in Yuma, Ariz. The field was divided into a "treated" seven acre portion and an "untreated" 11 acre portion. In both cases, identical procedures were employed with regard to the two fields, except, as discussed below, the treated field received the inventive composition. It had been noted in the past that the seven acres comprising the treated portion had never produced crops as well as the untreated 11 acre portion because of poor soil quality and soil salinity and wet ability problems.

In conducting the experiment, the following steps were performed.

1. Both fields were prepared for planting of cauliflower for seed production in double seed row bed configurations.
2. Both fields were watered in order to permit weed growth.
3. Six days after watering, the treated field only was irrigated with the inventive composition, comprising about 1 part SPER SAL to about 40 parts VAPAM, per acre. The untreated field was irrigated with VAPAM alone at the rate of 40 gallons per acre. Trough application was utilized in both cases. After irrigation, it was noted that the planter beds of the treated field were completely wetted, as opposed to those of the untreated field which displayed significantly less wetting.
4. Weeds, predominantly nutgrass, a notoriously difficult weed to control, were cultivated in the beds in both the treated and the untreated fields. It was observed that weed control of approximately 75% to 80% was accomplished in the untreated field, while weed control in excess of 96% was observed in the treated field. In fact, a weeding crew was required to remove the weeds not killed from the untreated field, prior to planting.
5. Cauliflower seeds were planted in a double seed row bed configuration in the treated and the untreated fields.
6. Irrigation water was applied, at uniform rates, to both the treated and untreated fields.

It will be noted that the only difference in the methods utilized for the two fields was in step 3, where the inventive composition was applied to the treated field.

During the growth period of the cauliflower, it was observed that there was a greater percentage of cauliflower germination, with more visually observable uniform plant population, after approximately three weeks in the treated field as compared to the untreated field.

At harvest, there was an increased yield of approximately 30% per acre from the treated field, as compared to the untreated field. In fact, the seven acre treated field produced substantially as much cauliflower seed as the untreated 11 acres. Thus, although the fields had been treated in a similar manner, throughout the experiment, with the single exception mentioned above, the yield from the field treated with the inventive composition was dramatically increased.

Another example of a method of using the inventive pesticide is to irrigate or otherwise apply SPER SAL to the field, following the germination of weed seeds. In this manner, an increased weed growth can be realized. In such cases, it is possible that a weed count of up to about 175 weeds per square foot could develop in a typical field, instead of only about 100 weeds per square foot which might be otherwise expected following the application of water only. Application of a substance such as VAPAM to the 175 weeds per square foot, at this point, weeds in a range which could vary from about 50% to 100%, depending on soil condition and other factors. In a given situation, such as in Example 1, assuming a weed kill rate of 80%, then the remaining 20% of the weeds, approximately 35 weeds per square foot, would produce a clearly unacceptable result, thereby rendering the soil unsuitable for some applications.

In a second example irrigation water and VAPAM are added to the soil, followed by an application of SPER SAL. In this case, the VAPAM would turn into a gas to fumigate the field. Approximately 80% of the weeds are killed. The field is then irrigated with SPER SAL and water. In this case, after the application of SPER SAL and water to the field, more weeds would be produced and the net result would be a case worse than the prior illustration.

However, by applying the inventive pesticide composition to the field, an overall weed kill rate of approximately 96% is realized. In this regard, only 7 weeds per square foot would remain, as compared to the 35 weeds surviving with the VAPAM treatment. Thus, the significant utility of the present invention is demonstrated.

EXAMPLE 2

In accordance with the general procedures of Example 1, Sper Sal, at rates of 0.5 and 1 quart per acre, was mixed with metam sodium (VAPAM) at 30 gallons of commercial product per acre and applied on a calcareous sandy loam soil in King County, Calif., to provide superior control of yellow nutsedge (*Cyperus esculentus*) and Johnsongrass (*Sorghum halepense*) compared to metam sodium alone, thirty days after the application of the treatments.

The experiments were carried out in a randomized block design with four replications; each plot was 140 feet long and 16 inches wide. VAPAM alone was applied to one plot, VAPAM plus Sper Sal was applied to two plots at different rates, while the fourth plot remained Untreated.

VAPAM (37% sodium methyl dithiocarbamate anhidrous) was shank-injected into the preformed beds previous to the planting of tomatoes at a rate equivalent to 30 gallons per acre followed by irrigation to seal the soil. Sper Sal (33% PMA) was added to two of the treatments at rates equivalent to 1.0 and 0.5 quarts per acre respectively.

The results of these tests, measured at different days after treatment (DAT), are shown in Table 1, below.

TABLE 1

Polymaleic Acid Improving the Herbicidal Activity of Metam Sodium in a Saline Soil in California, King County

| Treatment | Rate* G/A + Qt/A | Percentage Weed Control --Yellow Nutsedge-- | | | Johnsongrass |
|---|---|---|---|---|---|
| | | 7 DAT | 14 DAT | 33 DAT | 33 DAT |
| VAPAM | 30 | 50 | 30 | 0 | 17 |
| Va/Sper Sal | 30 + 1 | 83 | 90 | 67 | 80 |
| VA/Sper Sal | 30 + 0.5 | 77 | 92 | 72 | 90 |
| Untreated | -- + -- | 0 | 0 | 0 | 0 |

*VAPAM in gallons per acre (G/A), Sper Sal in quarts per Acre (Qt/A)

It will be seen from these data that the addition of Sper Sal at 0.5 or 1.0 quarts per acre induced a significant improvement in the herbicidal activity of metam sodium. The efficacy of control peaked 14 days after treatment for yellow nutsedge and was three times higher for both rates tested. The activity of metam sodium as a herbicide for yellow nutsedge control had ceased thirty days after the application when Sper Sal was not included and remained at levels above 60% on the Sper Sal treatments.

The single measurement done on Johnsongrass control thirty days after the application indicated the same pattern of response, with Sper Sal improving the weed control four times compared to VAPAM alone.

In addition to VAPAM, other commercially available equivalents are suitable as constituents of the present inventive composition. It should be noted that the term "pesticide" is well understood in the agricultural industry to include, but not limited to, herbicides, fungicides, nematocides and insecticides.

With regard now to the soil desalination constituent of the inventive composition, such a constituent is completely described in the foregoing mentioned patents and application Ser. No. 709,837, filed Jun. 4, 1991. When the inventive pesticide is used in soils containing a build up of salts and/or alkaline components, the desalination substance in the form of an anionic low molecular weight polymeric compound and/or organophosphorus compounds inactivates or removes the salts and/or alkaline components to help plants proliferate. It has been found that the capability of such compositions for inactivating or removing salts and/or alkaline components in sail is enhanced by the addition of surfactant, having surface active characteristics, which enhance micronutrient uptake by newly established plants.

The anionic polymeric materials for use in the present composition include polymers, copolymers and sulfonated polymers, and copolymers of acrylic acid, methacrylic acid, hydrolyzed polymers and copolymers of maleic anhydride and substantially neutral water soluble salts of these compounds.

In addition to these compounds, organophosphorus agents having a utility in soil treating include phosphonic acids as hydroxyethylidene diphosphonic acid, aminitri (methylenephosphonic) acid and nitrilo trismethylene triphosphonic acid, phosphonic acids such as phosphynocarboxylic acid, and substantially neutral salts of these acids. In a preferred form of the invention, the anionic compound is selected from the formulas consisting of:

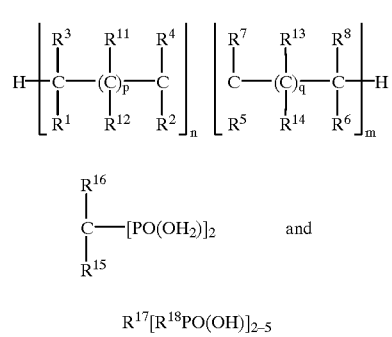

I

II

III wherein
the compounds of formula I have a molecular weight of from 300 to 5000 and
$R^1$ is hydroxyl, COOH, $C_6H_4$COOH, NHC(O)$R^9$—COOH, hydroxyphenol, COO$R^9$, SO$_3$H, $C_6H_4$SO3H, $R^9$SO$_3$H, COO$R^9$SO$_3$H, OSO$_3$H, $C_6H_4$OSO$_3$H, O$R^9$SO$_3$H, O$R^9$OSO$_3$H, OP(OH)$_2$, $R^9$P (OH)$_2$O, or phenyl, $R^2$ is hydrogen or COOH $R^3$ is hydrogen or $C_1$–$C_4$ alkyl $R^4$ is hydrogen or $C_1$–$C_4$ alkyl $R^5$ is hydrogen, COOH, $C_6H_4$COOH, NHC(O)$R^9$—COOH, hydroxyphenol, COO$R^9$, SO$_3$H, $C_6H_4$SO$_3$H, $R^9$SO$_3$H, COO$R^9$SO$_3$H, OSO$_3$H, $C_6H_4$OSO$_3$H, O$R^9$SO$_3$H, O$R^9$SO$_3$H, OP(OH)$_2$, $R^9$P(OH)$_2$O, phenyl, O$R^{10}$, hydroxyl or pyrrolidonyl;

$R_6$ is hydrogen or COOH;

$R^7$ is hydrogen or $C_1$–$C_4$ alkyl;

$R^8$ is hydrogen or $C_1$–$C_4$ alkyl;

$R^9$ is $C_1$–$C_4$ alkyl;

$R^{10}$ is $C_1$–$C_4$ alkyl;

$R^{11}$ is hydrogen or CH$_3$;

$R^{12}$ and $R^{13}$ are hydrogen;

$R^{14}$ is hydrogen or CH$_3$;

$R^{15}$ is hydrogen, hydroxyl or $C_1$–$C_4$ alkyl;

$R^{16}$ is hydrogen or $C_1$–$C_4$ alkyl;

$R^{17}$ is N, N$R^{19}$ N or N$R^9$N$R^9$N $R^{18}$ is $C_1$–$C_4$ alkyl;

$R^{19}$ is $C_1$–$C_4$ alkyl;

$R^1$ and $R^2$ when taken together are anhydride;

$R^5$ and $R^6$ when taken together are anhydride;

n and m are independently 3–100;

p and q are independently 0–3; and excluding anionic polymaleic anhydrides.

In addition to the compounds discussed above, other suitable compounds, more particularly disclosed in U.S. Pat. No. 4,923,500, as well as in the foregoing mentioned parent patent application Ser. No. 709,837, filed Jun. 4, 1991, incorporated herein by reference, are suitable. As indicated above, the addition of a surfactant can enhance the effectiveness of the inventive composition.

The present invention relates to a new use or method of making and using known compounds to achieve unexpected results. The compounds described above in detail are known to increase the solubility of sodium, potassium, calcium and magnesium salts by dispersing these salts so that an increased surface area is available to be wetted, thereby effectively shifting equilibrium from the solid phase to the dissolved liquid phase. It is believed that the precipitated salts are dispersed because the Helmholtz double layer model for dispersency is satisfied by the presence of the high negative charge densities of these compounds. Additionally, the precipitation of dissolved sodium, potassium, calcium and magnesium salts present in irrigation water is inhibited as soil dries. This is a result of crystal distortion effects at the surface of forming crystals. The net effect of both mechanisms (dispersency and crystal distortion) in soils is the removal of precipitated calcium salts from soil pore spaces.

The net effect of both mechanisms (dispersency and crystal distortion) in sodic alkaline soils is to provide excess calcium and magnesium cations to displace sodium from the colloidal clay surface resulting in sub-stoichiometrically induced cation exchange, facilitating the removal of sodium from the soil. The action of these discharges them through field tile drains, resulting in an improved drainage and percolation rate, reduction of soil salts and/or alkalis, improvement in the ability of the crops to absorb water and increased germination and yield.

It is to be understood that the above proposed mechanism is advanced only as a possible assistance in understanding the invention and that patentability is based on the novelty and utility of the composition and methods and not on the correctness of the mechanism proposed.

In addition to the uses of VAPAM discussed above, the product has utility for control of soilborne pests that attack ornamental, food and fibre crops: weeds and germinating weed seeds such as Annual Bluegrass, Bermudagrass, Chickweed, Dandelion, Ragweed, Henbit, Watergrass, Johnsongrass, Nutgrass and the like. In addition, the substance is effective in control of nematodes, centipedes and soilborne diseases such as Rhizoctiona, Pythrum, Phytophthora, Varticillium and Sclerotinia. In addition, the composition has utility as a fungicide for controlling fungus and other unwanted conditions such as crop Club Root of crucifers.

Prior to use, the composition of the present invention may be prepared by several techniques. In one technique, the pesticide and SPER SAL are tank mixed, either by a grower in the field or by a manufacturer at bulk plants. In such cases a ratio of about 1 part SPER SAL to about 40 parts pesticide, by volume, is suitable. It has been found that the two major constituents of the present invention may be safely combined, in varying relative proportions without any noticeable chemical reaction between the two.

Several methods of application of the present invention are suitable. These methods include applying the composition in a broadcast technique, utilizing a sprinkler system, utilizing flood irrigation and, in some applications by injecting the composition by side dressing into preformed plant beds and by means of drip irrigation systems, according to the manufacturer's label and recommendations and directions for use. In general, it is advisable to prepare the plant bed prior to application by breaking up soil clumps and by appropriate leveling and seeded bed preparation. Of course, it will be recognized that the inventive composition may be utilized for the treatment of plant beds after harvest to eradicate any crop left in the field after the harvesting operation has been completed.

In place of VAPAM in the inventive composition, the following substances can be used:

KERB, manufactured by Rhom & Haas, Philadelphia, Pa.

BALAN and TREFLAN, each manufactured by Elanco Products Company.

EPTAM, manufactured by ICI Americas, Wilmington, Del.

KERB is a water soluble pesticide, having broad applications for weed eradication. It comprises Pronamide 3, 5, dicloro-N-(1), 1-dimethyl-2(propynyl)-benzamide as the active ingredient (50%) combined with 50% inert ingredients. While the composition has significant utility in weed eradication, it also kills desirable plants. When KERB replaces VAPAM in the inventive composition, use of the composition results in improved weed eradication with a reduction in the phytotoxic effect sometimes seen when KERB alone applied, in high temperature conditions, to soils high in salt levels.

BALAN is a selective herbicide generally utilized for the preemergence control of annular grasses and broad leaf weeds. It has, as an active ingredient, N-butyl-N-ethyl-a, a, a trifluro-2, 6 dinitro-p-toluidine, 60%, combined with inert ingredients 40%. BALAN and TREFLAN are manufactured by Elanco Products Company. When BALAN and TREFLAN are combined with SPER SAL in the inventive composition, soil penetration is increased and a more effective weed eradication is realized than when BALAN or TREFLAN is used alone.

EPTAN, when utilized in place of VAPAM in the inventive composition, results in a pesticide having significantly improved soil diffusion characteristics than that observed in EPTAN when used alone.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed:

1. A pesticide composition for agricultural soils consisting essentially of water, a surfactant, a preemergent pesticide in a quantity sufficient to destroy unwanted organisms, and a soil desalinating substance in a quantity sufficient to reduce the salinity of the soil, said soil desalinating substance being selected from the formulas consisting of:

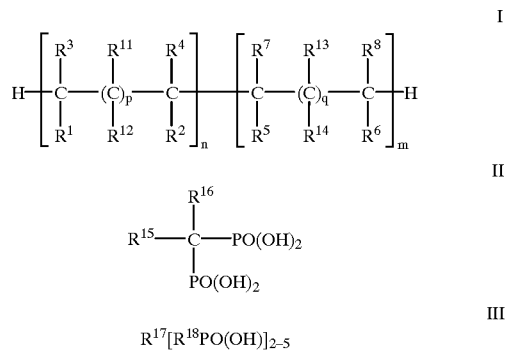

wherein:

the compounds of formula I have a molecular weight of from 300 to 5000;

$R^1$ is hydroxyl, COCH, $C_6H_4COOH$, $NHC(O)R^9COOH$, hydroxyphenyl, $COOR^9$, $SO_3H$, $C_6H_4SO_3H$, $R^9SO_3H$, $COOR^9SO_3H$, $OSO_3H$, $C_6H_4OSO_3H$, $OR^9SO_3H$, $OR^9OSO_3H$, $OP(OH)_2$, $R^9P(OH)_2O$, or phenyl;

$R^2$ is hydrogen or COOH;

$R^3$ is hydrogen or $C_1$–$C_4$ alkyl;

$R^4$ is hydrogen or $C_1$–$C_4$ alkyl;

$R^5$ is hydrogen, COOH, $C_6H_4COOH$, $NHC(O)R^9COOH$, hydroxyphenyl, $COOR^9$, $SO_3H$, $C_6H_4SO_3H$, $R^9SO_3H$, $COOR^9SO_3H$, $OSO_3H$, $C_6H_4OSO_3H$, $OR^9SO_3H$, $OR^9OSO_3H$, $OP(OH)_2$, $R^9P(OH)_2O$, phenyl, $OR^{10}$, hydroxyl or pyrrolidonyl;

$R^6$ is hydrogen or COOH;

$R^7$ is hydrogen or $C_1$–$C_4$ alkyl;

$R^8$ is hydrogen or $C_1$–$C_4$ alkyl;

$R^9$ is $C_1$–$C_4$ alkyl;

$R^{10}$ is $C_1$–$C_4$ alkyl;

$R^{11}$ is hydrogen or $CH_3$;

$R^{12}$ and $R^{13}$ are hydrogen;

$R^{14}$ is hydrogen or $H_3$;

$R^{15}$ is hydrogen, hydroxyl or $C_1$–$C_4$ alkyl;

$R^{16}$ is hydrogen or $C_1$–$C_4$ alkyl;

$R^{17}$ is N, $NR^{19}$ N or $NR^9NR^9N$ $R^{18}$ is $C_1$–$C_4$ alkyl;

$R^{19}$ is $C_1$–$C_4$ alkyl;

$R^1$ and $R^2$ when taken together are anhydride;

$R^5$ and $R^6$ when taken together are anhydride;

n and m are independently 3–100; and p and q are independently 0–3; wherein the ratio of the volume of said pesticide to the total volume of water, surfactant, and soil desalinating substance is about 40 to 1.

2. A composition of claim 1 wherein said pesticide is selected from the group consisting of N-butyl-N-ethyl-α,α,α-trifluoro-2,6-dinitro-p-toluidine; α,α,α-trifluoro-2,6-dinitro-N,N-dipropyl-p-toluidine; 3,5, dicloro-N-(1), 1-dimethyl-2(propynyl)-benzamide; sodium methyldithiocarbamate; and S-ethyl dipropylthiocarbamate.

3. A composition of claim 2 wherein said pesticide is sodium methyldithiocarbamate.

4. A composition of claim 3 wherein said surfactant is triethanolamine dodecybenzenesulfonate and said desalinating substance comprises an aqueous solution of polymaleic acid.

5. A method for eradicating crop plants from a harvested field comprising:
   (a) harvesting said crop from the field; and
   (b) applying to said field a pesticide in combination with a desalinating substance having a formula selected from the group consisting of:

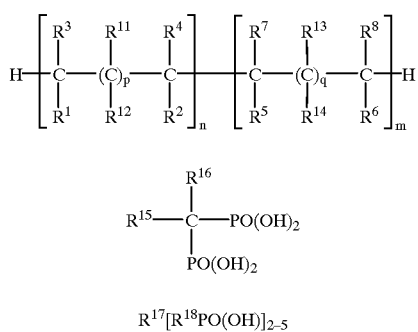

wherein:

the desalinating substance of formula I has a molecular weight of from 300 to 5000;

$R^1$ is hydroxyl, COOH, $C_6H_4COOH$, NHC(O)$R^9$COOH, hydroxyphenyl, COOR$^9$, SO$_3$H, $C_6H_4SO_3BH$, $R^9SO_3H$, COOR$^9SO_3H$, OSO$_3H$, $C_6H_4OSO_3H$, OR$^9SO_3H$, OR$^9OSO_3H$, OP(OH)$_2$, $R^9P(OH)_2O$, or phenyl;

$R^2$ is hydrogen or COOH;

$R^3$ is hydrogen or $C_1$–$C_4$ alkyl;

$R^4$ is hydrogen or $C_1$–$C_4$ alkyl;

$R^5$ is hydrogen, COOH, $C_6H_4COOH$, NHC(O)$R^9$COOH, hydroxyphenyl, COOR$^9$, SO$_3$H, $C_6H_4SO_3H$, $R^9SO_3H$, COOR$^9SO_3H$, OSO$_3H$, $C_6H_4OSO_3H$, OR$^9SO_3H$, OR$^9OSO_3H$, OP(OH)$_2$, $R^9P(OH)_2O$, phenyl, OR$^{10}$, hydroxyl or pyrrolidonyl;

$R^6$ is hydrogen or COOH;

$R^7$ is hydrogen or $C_1$–$C_4$ alkyl;

$R^8$ is hydrogen or $C_1$–$C_4$ alkyl;

$R^9$ is $C_1$–$C_4$ alkyl;

$R^{10}$ is $C_1$–$C_4$ alkyl;

$R^{11}$ is hydrogen or $CH_3$;

$R^{12}$ and $R^{13}$ are hydrogen;

$R^{14}$ is hydrogen or $CH_3$;

$R^{15}$ is hydrogen, hydroxyl or $C_1$–$C_4$ alkyl;

$R^{16}$ is hydrogen or $C_1$–$C_4$ alkyl;

$R^{17}$ is N, NR$^{19}$N or NR$^9$NR$^9$N $R^{18}$ is $C_1$–$C_4$ alkyl;

$R^{19}$ is $C_1$–$C_4$ alkyl;

$R^1$ and $R^2$ when taken together are anhydride;

$R^5$ and $R^6$ when taken together are anhydride;

n and m are independently 3–100; and p and q are independently 0–3.

6. A method of claim 5 wherein said pesticide is selected from the group consisting of N-butyl-N-ethyl-α,α,α-trifluoro-2,6-dinitro-p-toluidine; α,α,α-trifluoro-2,6-dinitro-N,N-dipropyl-p-toluidine; 3,5, dichloro-N-(1), 1-dimethyl-2(propynyl)-benzamide; sodium methyldithiocarbamate; and S-ethyl dipropylthiocarbamate.

7. A method of claim 6 wherein said pesticide is sodium methyldithiocarbamate and wherein said pesticide is converted into a gaseous fumigant following application.

8. A method of claim 5 wherein said pesticide is sodium methyldithiocarbamate and wherein said pesticide is applied in combination with a surfactant.

9. A method of claim 8 wherein said surfactant is triethanolaminedodecylbenzenesulfonate and said desalinating substance comprises polymaleic acid.

* * * * *